United States Patent [19]

Giobbio et al.

[11] Patent Number: 4,985,549

[45] Date of Patent: Jan. 15, 1991

[54] PROCESS FOR PREPARING AMIKACIN

[75] Inventors: Vincenzo Giobbio, Turin; Leonardo Ambrosini, Bergamo, both of Italy

[73] Assignees: Chementecno S.r.l., Milan; Irca Industrie Ricerche Chimiche D'Albano S.p.A., Bergamo, both of Italy

[21] Appl. No.: 472,262

[22] Filed: Jan. 30, 1990

[30] Foreign Application Priority Data

Sep. 22, 1989 [IT] Italy .................. 21794 A/89

[51] Int. Cl.$^5$ .................. C07H 15/22
[52] U.S. Cl. .................. 536/13.8; 536/18.5; 536/13.7; 536/124
[58] Field of Search .................. 536/13.7, 13.8, 18.5

[56] References Cited

U.S. PATENT DOCUMENTS

| 4,136,254 | 1/1979 | Nagabhushan et al. | 536/13.8 |
| 4,230,847 | 10/1980 | Nagabhushan et al. | 536/13.8 |
| 4,242,331 | 12/1980 | Gase et al. | 536/13.8 |
| 4,297,485 | 10/1981 | Umezana et al. | 536/13.8 |
| 4,547,492 | 10/1985 | Umezawa et al. | 536/13.8 |

OTHER PUBLICATIONS

The Journal of Antibiotics, vol. XXV, No. 12, pp. 695-708, Kawaguchi et al., BB-K8, New Semisynthetic Aminoglycoside Antibiotic.

*Primary Examiner*—Johnnie R. Brown
*Assistant Examiner*—Elli Peselev
*Attorney, Agent, or Firm*—Oblon, Spivak, McClelland, Maier & Neustadt

[57] ABSTRACT

Described is a process for preparing Amikacin wherein 1-N-(L(—)-γ-benzyloxycarbonylamino-α-hyroxybutyryl)-3,6'-di-N-benzyloxycarbonyl-Kanamycin A suspended in a suitable solvent, is treated with an aqueous solution of formic acid in the presence of a catalyst; the reaction mixture is charged on a ion exchange resin column to yield the desired product. Among the side-products Kanamycin A is obtained which is per se useful.

9 Claims, No Drawings

PROCESS FOR PREPARING AMIKACIN

DESCRIPTION

The present invention relates to a process for preparing Amikacin, otherwise named as 1-N-(L(−)-γ-amino-α-hydroxy-butyryl)Kanamycin A, having the following formula (I)

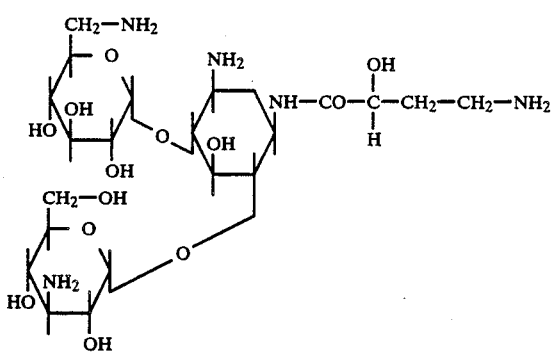

starting from 1-N-(L(−)-γ-benzyloxycarbonylamino-α-hydroxy-butyryl)-3,6'-di-N-benzyloxycarbonyl-Kanamycin A (II)

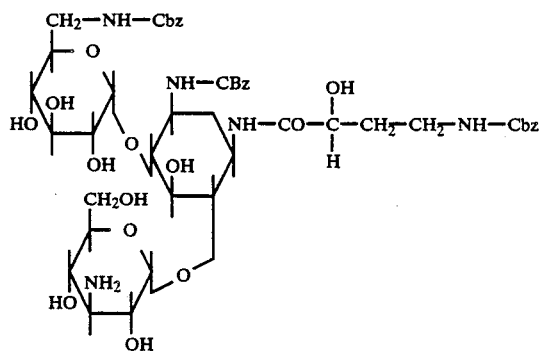

and formic acid.

Amikacin is a known aminoglycoside antibiotic derived from Kanamycin, and showing broad action spectrum and strong resistance against the enzymes inactivating the other aminoglycoside antibiotics. The synthesis of compound (I) is described by literature (e.g., J. Antibiotic, 1972, 25, 695), and by the patent DE No. 2,234,315.

All of the known processes for preparing Amikacin are based on the selective protection of the amino groups in 3-6'- and 3"-position of Kanamycin A (III)

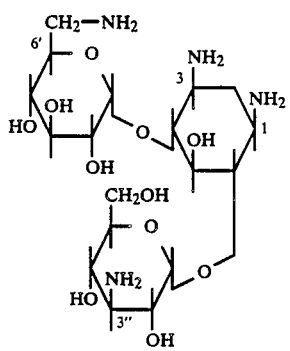

the so obtained intermediate being sequentially reacted with L-(−)-2-hydroxy-4-aminobutyroyl radical, and de-protected for yielding the desired compound (I).

The use of 1-N-(L(−)-γ-benzyloxycarbonylamino-α-hydroxy-butyryl)-3,6'-di-N-benzyloxycarbonyl-Kanamycin A (II) for producing compound (I) is known. In fact, de-protecting (II) the desired compound (I) can be obtained according to scheme (A) shown below:

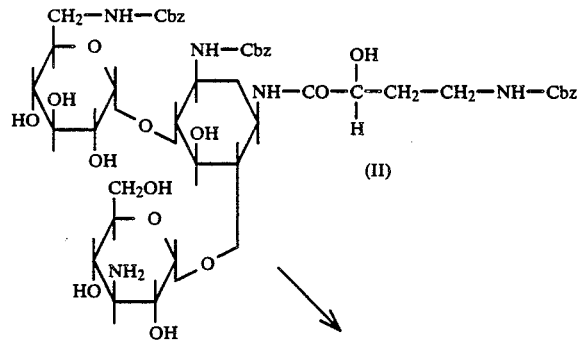

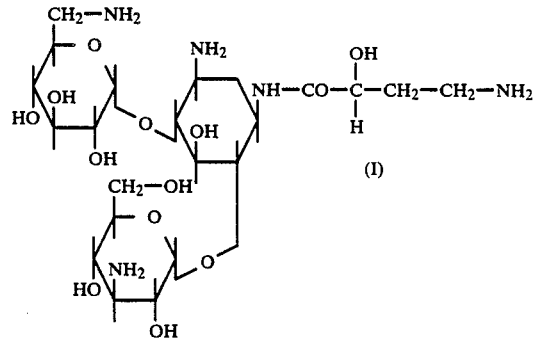

SCHEME A

Specifically U.S. Pat. Nos. 4,230,847, 4,297,485, and 4,136,254 describe the de-protection of compound (II) by means of hydrogen in the presence of palladium on charcoal (Pd/C) (titer 5%) in aqueous methanol, aqueous dioxane or other organic solvents. This method is not very convenient when applied on industrial scale, because it needs special appartus for hydrogenation at a pressure different from the atmospheric one, and for carrying out such reaction according to safety rules.

Furthermore the de-protection by catalytic hydrogenation can give good yields of compound (I) providing that compound (II) to be hydrogenated is sufficiently devoid of impurities, mostly consisting of benzyloxycarbonyl derivatives of amino groups different from the ones in 3- and 6'-position of Kanamycin A, or of poly(benzyloxycarbonyl) derivatives of Kanamycin A, or of traces of sulphurate compounds.

It has been now surprisingly found that employing formic acid as nascent hydrogen donor, in the presence of a suitable catalyst for de-protecting compound (II), good yields of (I) are obtained with no need of special pressure apparatus for hydrogenation, and with no need of reacting a specifically purified compound (II) (crude compound) to obtain quantitative yields of product. This is particularly important in view of an industrial production.

Another advantageous feature of the present invention resides in the possibility to completely remove all the benzyloxycarbonyl protecting groups by treatment with formic acid, thus all the reaction impurities can be converted in Kanamycin A, which can be eventually recovered as fraction of the eluate obtained after percolation of the reaction mixture through a ion exchange resin column.

More particularly, the present invention relates to a process for preparing Amikacin (I), wherein 1-N-(L(−)-γ-benzyloxycarbonylamino-α-hydroxybutyryl)-3,6'-di-N-benzyloxycarbonyl-Kanamycin A (II) is suspended in a ratio of from 1:5 to 1:25 in a solvent selected from the group consisting of alcohols, ketones, dimethylformamide, acetonitrile, aliphatic esters, hydrocarbons, chlorinated solvents and water; after addition of a suitable catalyst selected from the group consisting of Pt/C, mixtures of Pd/C and Ni-Raney, and Pd/C (title 2.5%) in an amount equal about to the weight of compound (II), an aqueous solution of formic acid from 10% to 100% is slowly added at a temperature between 0° and 100° C. in a ratio of 1:1 to compound (II), the reaction mixture containing product (I) and Kanamycin A being percolated through a ion exchance resin column by eluting with a 2N NH$_3$ solution, the fraction of compound (I) being separated and the solvent evaporated under reduced pressure.

In the process described in the present invention, the preferred solvent for suspending compound (II) is water, and it is preferably employed in a ratio of 1:10. The reaction is preferably carried out at a temperature of 20°-25° C., while adding an aqueous solution of formic acid, preferably 25%, in a period of about 8 hours, in the reaction mixture. As catalyst, Pt/C, mixtures of Pd/C and Ni-Raney, and more advantageously Pd/C (2.5%) are employed.

It is advisable, but not necessary, to use a surfactant, preferably selected from the group of polysiloxane compounds, for avoiding the formation of abundant foam during the reaction, which is due to the loss of $CO_2$.

By means of percolation of the final reaction mixture through a suitable ion exchange resin column, preferably a weakly acidic ion exchange resin such as Amberlite IRC-76, Dowex CCR-2, Kastel C-101, more advantageously Amberlite CG-50 (Rohm and Haas Co.), and of elution with a 2N NH$_3$ solution, the method described in the present invention affords the separation of the fractions corresponding to product (I) and Kanamycin A which can be then recovered and recycled for another synthesis of product (I).

The following examples illustrate, but do not limit the present invention.

EXAMPLE 1

To a suspension of 9.87 g of 1-N-(L(−)-γ-benzyloxycarbonyl-amino-α-hydroxybutyryl)-3,6'-di-N-benzyloxycarbonyl-Kanamycin A in deionized water (120 ml), 0.4 ml of surfactant (ANTIFOAM ER 20, produced and marketed by Eingenmann & Veronelli S.p.A.) and 9.8 g of Pd/C (2.5%) are added. The mixture is stirred under a light flow of N$_2$ and a solution of 9.9 ml of formic acid in 30 ml of deionized water is added dropwise in 8 hours at a temperature of 20°-25° C. After said addition, the stirring is maintained for further 8 hours at 20°-25° C.

The reaction mixture is then filtrated under reduced pressure and percolated through an Amberlite CG-50 column in glass (8 cm of diameter and 1 m height). By eluting with a 2N NH$_3$ solution, the two fractions corresponding to Amikacin and Kanamycin A are separated.

Evaporating under reduced pressure the fraction containing Amikacin, 5.8 g of pure product are obtained.

EXAMPLE 2

25 g of crude 1-N-(L(−)-γ-benzyloxycarbonylamino-α-hydroxybutyryl)-3,6'-di-N-benzyloxycarbonyl-Kanamycin A (tit. 55%) are suspended in deionized water (170 ml), and 0.6 ml of surfactant (ANTIFOAM ER 20) and 25 g of Pd/c (2.5%) are added therein.

While stirring under light flow of N$_2$, a solution of 25 ml of formic acid in 100 ml of deionized water is added dropwise in 8 hours at a temperature of 20°-25° C. The reaction mixture is maintained under stirring at 20°-25° C. for further 8 hours.

After filtration under reduced pressure, the filtrate is washed with a small amount of deionized water. Operating a described in Example 1, 8.1 g of Amikacin and, after evaporation of the corresponding fraction under reduced pressure, 1.2 g of Kanamycin A are obtained.

EXAMPLE 3

5 kg of crude 1-N-(L(−)-γ-benzyloxycarbonylamino-α-hydroxybutyryl)-3,6'-di-N-benzyloxycarbonyl-Kanamicyn A (tit. 62%) are suspended in deionized water (60 l). After addition of 150 ml of surfactant (ANTIFOAM ER 20) and 5 kg of Pd/C (2,5%), the reaction mixture is stirred under a light flow of N$_2$ for 8 hours, while maintaining the temperature at 20°-25° C. After addition of a solution of 5 l of formic acid in 15,5 l of deionized water, the reaction mixture is still maintained under stirring at 20°-25° C. for 8 hours. It is filtered under reduced pressure and washed with a small amount of deionized water.

The reaction mixture is percolated through a glass column (40 cm of diameter and 5 m height) charged with Amberlite CG-50. After elution with a 2N NH$_3$ solution, the two fractions are separated and, after evaporation under reduced pressure, 2.95 kg of Amikacin and 0.3 kg of Kanamycin A are obtained respectively.

We claim:

1. A process for preparing Amikacin (I), wherein 1-N-(L-(−)-α-benzyloxycarbonylamino-α-hydroxybutyryl)-3,6'-di-N-benzyloxycarbonyl-Kanamycin A (II) is suspended in a ratio of from 1:5 to 1:25 in a solvent selected from the group consisting of alcohols, ketones, dimethylformamide, acetonitrile, aliphatic esters, hydrocarbons, chlorinated solvents and water; after addition of a suitable catalyst selected from the group consisting of Pt/C, mixtures of Pd/C and Ni-Raney, and Pd/C in an amount equal to about the weight of compound (II), an aqueous solution of formic acid from 10% to 100% is slowly added at a temperature between 0° and 100° C. in a ratio of about 1:1 with compound (II), the reaction mixture containing product (I) and Kanamycin A being percolated through a ion exchange resin column by eluting with a 2N NH$_3$ solution, the fraction of compound (I) being separated and the solvent evaporated under reduced pressure.

2. Process according to claim 1, wherein compound (II) is suspended in water.

3. Process according to claim 2, wherein compound (II) is suspended in water in a ratio of 1:10.

4. Process according to claim 1, wherein the reaction is carried out at a temperature of 20°–25° C.

5. Process according to claim 1, wherein an aqueous 25% formic acid solution is employed.

6. Process according to claim 1, wherein the catalyst is Pd/C (titer 2.5%).

7. Process according to claim 1, wherein a surfactant selected from the group consisting of polysiloxane derivatives is employed.

8. Process according to claim 1, wherein the ion exchange resin is selected from the group consisting of weakly acidic ion exchange resin.

9. Process according to claim 1, wherein the fraction of the eluate consisting of Kanamycin A is separated and evaporated under reduced pressure.

* * * * *